(12) United States Patent
St. Laurent et al.

(10) Patent No.: US 8,802,885 B2
(45) Date of Patent: Aug. 12, 2014

(54) PROCESS FOR PREPARING 3-METHYLSULFONYLPROPIONITRILE

(71) Applicant: Olatec Industries LLC, Rye Brook, NY (US)

(72) Inventors: Joseph P. St. Laurent, Lakeville, MA (US); Gerald S. Jones, Norwood, MA (US); David M. Bresse, Middleboro, MA (US)

(73) Assignee: Olatec Industries LLC, Rye Brook, NY (US)

( * ) Notice: Subject to any disclaimer, the term of this patent is extended or adjusted under 35 U.S.C. 154(b) by 0 days.

(21) Appl. No.: 13/777,754

(22) Filed: Feb. 26, 2013

(65) Prior Publication Data

US 2013/0225865 A1     Aug. 29, 2013

Related U.S. Application Data

(60) Provisional application No. 61/603,744, filed on Feb. 27, 2012.

(51) Int. Cl.
*C07C 255/03*     (2006.01)

(52) U.S. Cl.
USPC ........................................ 558/303

(58) Field of Classification Search
None
See application file for complete search history.

(56) References Cited

U.S. PATENT DOCUMENTS

| | | | |
|---|---|---|---|
| 4,424,167 A | 1/1984 | Oeckl | |
| 4,476,137 A | 10/1984 | Haviv et al. | |
| 4,536,599 A | 8/1985 | Masuko et al. | |
| 5,175,192 A | 12/1992 | Ulrich et al. | |
| 5,348,838 A | 9/1994 | Ushirogouchi et al. | |
| 6,551,615 B1 | 4/2003 | Iyer et al. | |
| 8,476,316 B2 | 7/2013 | St. Laurent | |
| 2006/0069160 A1 | 3/2006 | Torrence | |
| 2007/0293457 A1 | 12/2007 | Baker et al. | |
| 2009/0291917 A1 | 11/2009 | Akama et al. | |
| 2010/0221336 A1 | 9/2010 | Fink et al. | |
| 2010/0240756 A1 | 9/2010 | St. Laurent | |

FOREIGN PATENT DOCUMENTS

| | | |
|---|---|---|
| EP | 355049 A2 | 2/1990 |
| WO | WO 2007080382 A1 * | 7/2007 |

OTHER PUBLICATIONS

Bell et al. J.C.S. Perkins I (1981) 2106-2115.*
International Search Report and Written Opinion of PCT Application No. PCT/US2013/027749 with a mailing date of Jun. 18, 2013.
Armesto et al.: "First Steps in the Oxidation of Sulfur-Containing Amino Acids by Hypohalogenation: Very Fast Generation of Intermediate Sulfenyl Halides and Halosulfonium Cations". Tetrahedron 56 (2000) p. 1103-1109.
Hsi et al.: "Synthesis of Some Analogs of Rorifone", Scientia Sinica, vol. 27, No. 6, Dec. 1974.

* cited by examiner

*Primary Examiner* — Nyeemah A Grazier
(74) *Attorney, Agent, or Firm* — Perkins Coie LLP; Viola T. Kung

(57) ABSTRACT

The present invention relates to processes for preparing 3-methylsulfonylpropionitrile. The processes provide a good yield and a good purity of the final product and provide a controllable reaction. The present invention also relates to a crystalline form of 3-methylsulfonylpropionitrile having X-ray diffraction peaks at 13.9±0.1, 19.2±0.1, 20.0±0.1, 22.5±0.1, 23.2±0.1, 25.7±0.1, 28.1±0.1, 29.9±0.1, and 30.6±0.1 degrees 2θ, and wherein the most intense peak is the peak at 13.9±0.1 degrees 2θ.

10 Claims, 9 Drawing Sheets

Recrystallization

| 5 L Reactor |
|---|
| 1. Add EtOH |
| 2. Add crude product cake |
| 3. Heat to 60-65°C to dissolve |
| 4. Cool to 5-10°C over 1½-2 hr |
| 5. Stir 30-60 min at 5-10°C |

FIG. 1C (Continued)

PROCESS FOR PREPARING 3-METHYLSULFONYLPROPIONITRILE

This application claims the benefit of U.S. Provisional Application No. 61/603,744, filed Feb. 27, 2012; which is incorporated herein by reference in its entirety.

FIELD OF THE INVENTION

The present invention relates to processes for preparing 3-methylsulfonylpropionitrile. The present invention also relates to a crystalline form of 3-methylsulfonylpropionitrile.

BACKGROUND OF THE INVENTION

3-Methylsulfonylpropionitrile (CAS Registry 54863-37-5) is useful for treating inflammation and pain as described in U.S. Publication No. 2012-0157524, which is incorporated herein by reference in its entirety.

There is a need for efficient processes for preparing the 3-methylsulfonylpropionitrile, particularly in a large scale of over 1 Kg.

SUMMARY OF THE INVENTION

The present invention is directed to methods for preparing 3-methylsulfonylpropionitrile. In one method, the method comprises the steps of: (a) reacting 3-bromopropionitrile and sodium methylsulfinate in an organic solvent to obtain crude 3-methylsulfonylpropionitrile in a solid form, and (b) removing a byproduct sodium bromide.

In an alternative method, the method comprises the steps of: (a) reacting 3-bromopropionitrile and sodium thiomethoxide in a first aqueous solution to form methylthiopropionitrile, (b) separating the reaction mixture of (a) into an aqueous phase and an organic phase and collecting the organic phase, (c) isolating methylthiopropionitrile in the organic phase, (d) mixing the isolated methylthiopropionitrile with acetic anhydride, (e) reacting the mixture of (d) with a second aqueous solution comprising acetic acid, acetic anhydride and hydrogen peroxide at 25-42° C. to form 3-methylthiopropionitrile, and (f) isolating 3-methylsulfonylpropionitrile from the reaction mixture of (e).

The present invention is further directed to a crystalline form of 3-methylsulfonylpropionitrile having X-ray diffraction peaks at 13.9±0.1, 19.2±0.1, 20.0±0.1, 22.5±0.1, 23.2±0.1, 25.7±0.1, 28.1±0.1, 29.9±0.1, and 30.6±0.1 degrees 2θ, and wherein the most intense peak is the peak at 13.9±0.1 degrees 2θ.

BRIEF DESCRIPTION OF THE DRAWING

FIG. 1A-1C illustrate a flow chart for preparing 3-methylsulfonylpropionitrile according to Example 1.

DETAILED DESCRIPTION OF THE INVENTION

Figure 1A:
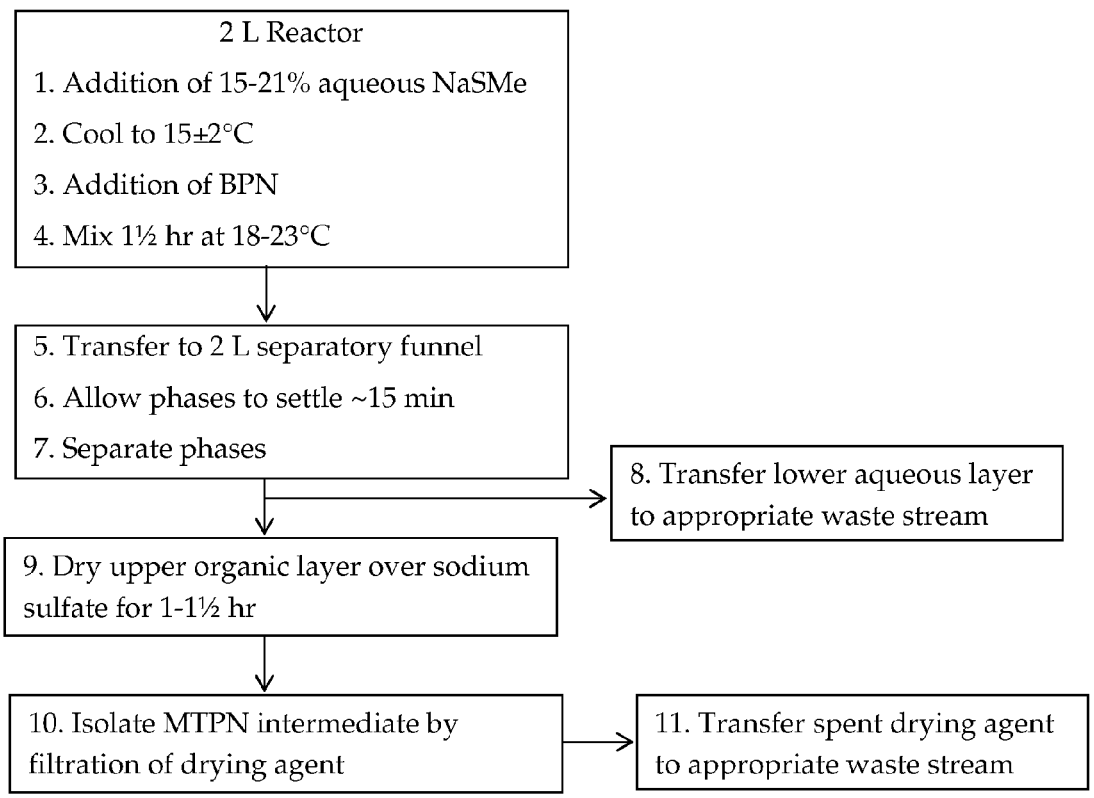

The present invention relates to processes for preparing purified compound of 3-methylsulfonylpropionitrile:

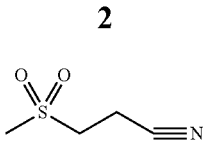

The process of the present invention is either a one-step reaction or two-step reactions. The process is suitable for large-scale production (over 1 Kg, preferably over 2 Kg, over 4 Kg, or over 10 Kg). The process provides good yield of ≥75%, preferably ≥80%, or ≥85%. The process provides purity of 3-methylsulfonylpropionitrile ≥80%, preferably ≥85%, or ≥90%, or ≥95%, or ≥98%.

One-Step Reaction

The present invention is directed to a method for preparing 3-methylsulfonylpropionitrile. The method comprises the steps of:

(a) reacting 3-bromopropionitrile (BPN) and sodium methylsulfinate in an organic solvent to obtain crude 3-methylsulfonylpropionitrile in a solid form, and (b) removing a byproduct sodium bromide.

The method optionally comprises a step (c) after step (b):

(c) purifying 3-methylsulfonylpropionitrile.

In step (a), the crude 3-methylsulfonylpropionitrile is prepared via a one-step synthetic route involving alkylation of methanesulfinic acid sodium salt with 3-bromopropionitrile.

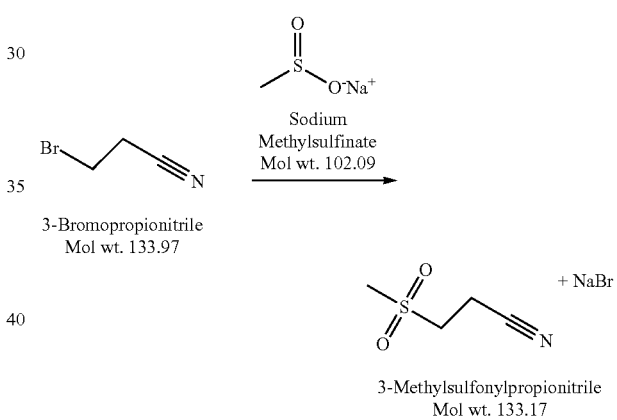

An organic solvent is used in the reaction to facilitate the alkylation and enable isolation of a crude product filter cake (mixture of 3-methylprpionitrile and sodium bromide NaBr). Examples of suitable organic solvents include ethanol, methanol, propanol, isopropanol, butanol, or a mixture thereof. Preferred organic solvent is ethanol, or a mixture of alcoholic solvents containing ethanol (e.g., ethanol/methanol/isopropanol at 90/5/5).

In general, 3-bromopropionitrile is utilized in a molar excess over sodium methylsulfinate to avoid the isolation of a final product from an impurity associated with the sodium methylsulfinate starting material. For example, 3-bromopropionitrile is typically in 10-30% molar excess (e.g., 20% molar excess) over methylsulfinate.

In general, the reaction is carried at a temperature higher than ambient temperature to accelerate the reaction rate. Preferably, the reaction is carried at ≥40° C., or ≥50° C., or ≥60° C., or ≥70° C. For example, when ethanol is used as the solvent medium, the reaction temperature is in general 74-83° C., preferably 75-81° C.

The reaction time should be sufficient to allow the reaction to go to completion. In general, the reaction time is at least 8 hours, for example, 8-48 hours, preferably 14-20 hours, or 16-18 hours. Upon completion of the reaction, the reaction mixture contains a mixture of solids: the product 3-methylsulfonylpropionitrile, NaBr and residual BPN.

After the reaction, the crude 3-methylsulfonylpropionitrile is obtained in a solid form from the reaction mixture. In one embodiment, the reaction mixture is cooled to ≤15° C. (preferably ≤10° C., or 1-9° C.) to increase the precipitation of 3-methylsulfonylpropionitrile from the reaction mixture. The cooling period is preferably over 1 hour, or 2 hours. The reaction mixture is then filtered and the crude 3-methylsulfonylpropionitrile is in a form of damp filter cake, which also contains NaBr and trace residual BPN. Most of the excess BPN is removed by filtration and appears in the filtrate. The damp filter cake is optionally washed with the same organic solvent and dried under vacuum.

In step (b), the byproduct sodium bromide is removed by (i) adding acetone to the filter cake to dissolve the solid and form a solution, (ii) filtering the solution to remove an insoluble byproduct, and (iii) collecting the filtrate. 3-methylsulfonylpropionitrile is soluble in acetone, whereas the byproduct sodium bromide is insoluble in acetone. After filtration, the insoluble sodium bromide is removed from the acetone filtrate that contains the product 3-methylsulfonylpropionitrile and trace BPN. Other solvents in which the product is soluble but NaBr is not (e.g., tetrahydrofuran or dichloromethane) may be used instead of acetone. However, acetone is a preferred solvent because of the relative high solubility of the product in acetone. In addition, acetone does not form an oxidation byproduct, and it is easy to be removed.

In the optional step (c), 3-methylsulfonylpropionitrile is further purified to remove trace BPN in the acetone filtrate, by concentrating the acetone filtrate, dissolving the dried material in a suitable organic solvent, and crystallizing 3-methylsulfonylpropionitrile.

In one embodiment, the product-rich filtrates are concentrated to dryness via vacuum distillation and then dissolved in an organic solvent suitable for crystallization of the product.

In another embodiment, the acetone in the acetone filtrate is replaced with an organic solvent having a higher boiling temperature than acetone and in which the product is soluble, by heating the acetone filtrate and adding the organic solvent in increments. For example, the acetone filtrate is transferred to a large jacketed reactor and acetone is removed under reduced pressure while heating with the concomitant addition of ethanol. At the end of this step, the reactor contains a hot ethanolic solution of product and trace residual BPN. As the hot ethanolic solution cools, crystalline product begins to precipitate. The mixture is further cooled, for example, to ≤10° C., to complete the precipitation process. The crystalline product is essentially devoid of residual BPN (<0.02%), which remains in the liquid and is removed by the crystallization step.

Two-Step Reactions

The process comprises the steps of: (a) reacting bromopropionitrile and sodium thiomethoxide (NaSMe) in a first aqueous solution to form methylthiopropionitrile, (b) separating the reaction mixture of (a) into an aqueous phase and an organic phase, (c) isolating methylthiopropionitrile in the organic phase, (d) mixing the isolated methylthiopropionitrile with acetic anhydride, (e) reacting the mixture of (d) with a second aqueous solution comprising acetic acid, acetic anhydride and hydrogen peroxide at 25-42° C. to form methylsulfonylpropionitrile, and (f) isolating methylsulfonylpropionitrile from the reaction mixture of (e).

The inventors have discovered that by reacting bromopropionitrile and sodium thiomethoxide in an aqueous solution, the intermediate methylthiopropionitrile formed can be easily separated from other reagents. The inventors also discovered that the two-step oxidation of the intermediate methylthiopropionitrile (steps (d) and (e)) in a temperature 25-42° C. provides a controlled reaction and a good yield of the final product.

The reaction step (a) is an alkylation step, which reacts bromopropionitrile and sodium thiomethoxide (NaSMe) in an aqueous solution to form an intermediate methylthiopropionitrile.

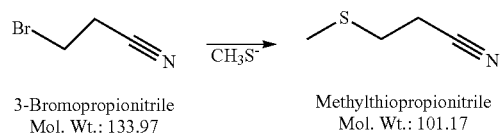

3-Bromopropionitrile
Mol. Wt.: 133.97

Methylthiopropionitrile
Mol. Wt.: 101.17

The alkylation reaction is typically carried out at 10-25° C., preferably 10-20° C. The reaction time is 1-4 hours, preferably 2-3 hours. In one embodiment, liquid 3-bromoproprionitrile is added to an aqueous solution of sodium thiomethoxide (e.g., 14-21% w/w). The alkylation is carried out in an aqueous solution instead of an organic solvent such as an alcohol. The aqueous solution facilitates an easy isolation of the intermediate methylthiopropionitrile (MTPN) from other reagents that remain in the aqueous phase. 3-bromopropionitrile is used in the alkylation reaction instead of 3-chloropropionitrile because (a) Br is more reactive toward substitution than Cl, and (b) Br reagent (HMIS health hazard rating=2) is less hazardous than Cl reagent (HMIS health hazard rating=4).

After the alkylation step, the reaction mixture is allowed to settle and to separate into two phases: a lower aqueous phase and an upper organic phase containing MTPN. MTPN, which is less dense than water, accumulates in a layer above the surface of the water. Excess methylthiomethoxide and sodium bromide byproduct remain in the aqueous phase. The lower aqueous layer is discarded, and the upper organic phase of MTPN is obtained. The organic phase is optionally dried over solid sodium sulfate to remove residual water and water soluble salts. The dried MTPN is isolated (for example, by vacuum filtration) as a clear oily liquid.

The intermediate MTPN is then oxidized to form the final product of 3-methylsulfonylproprionitrile.

The inventors discovered that one-pot oxidation of MTPN to sulfoxide (—SO—) and subsequent sulfone (—SO$_2$—) in acetic acid, acetic anhydride, and hydrogen peroxide solution, as shown below, was extremely difficult to control in the scale of hundred grams.

One-Pot Oxidation

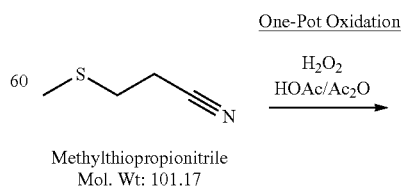

Methylthiopropionitrile
Mol. Wt: 101.17

-continued

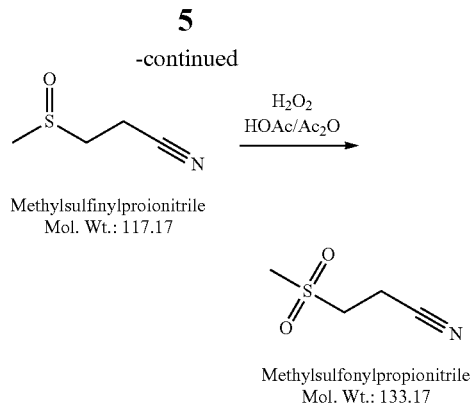

An induction period was noticed before the initiation of the second oxidation (sulfoxide to the sulfone). At this point, heat evolution ceased and the pot temperature rapidly decreased. After warming the reactor gently to induce oxidation, the temperature steadily increased due to the exothermic oxidation, even though the jacket recirculator was at maximum cooling capacity. The evolution of heat continued to increase and the reaction temperature was not controllable.

To remedy this situation, the inventors have discovered two-step procedures, by which the reaction is controlled and the yield of the final product is improved. In the present invention, the oxidation is carried out by two steps: (d) mixing MTPN with acetic anhydride, and (e) reacting the mixture of (d) with an aqueous solution comprising acetic acid, acetic anhydride and hydrogen peroxide at 25-42° C. to form the final product 3-methylsulfonylpropionitrile (MSPN). The reaction time is in general 1-4 hours, preferably 1-3 hours, or 1-2 hours In one embodiment, the MTPN is mixed with acetic anhydride at a molar ratio of 1:1-3, preferably about 1:2, and then slowly added to the reactor containing acetic acid, acetic anhydride and aqueous hydrogen peroxide (e.g., 20-40% w/v) while maintaining the temperature at 25-42° C., preferably 28-40° C., and more preferably 30-35° C. The two-step procedures eliminate the induction period and allow the reaction temperature to be controlled.

After the oxidation reaction is completed, the final product MSPN is isolated from the reaction mixture by removing acetic acid and residual hydrogen peroxide. In one embodiment, the acetic acid and residual hydrogen peroxide are removed by distillation and/or rotary evaporation. After concentration, the product is mixed with ethanol, heated and then cooled to 5-10° C. to effect crystallization. The product can be isolated by vacuum filtration and washed with cold ethanol. The typical yield of the crystalline MSPN material from the oxidation of the intermediate MTPN is about 90%. The typical overall yield of the crystalline MSPN material from the starting materials is about 76-80%.

Crystalline Form

3-Methylsulfonylpropionitrile is recrystallized using solvents of varying polarity to determine if the material exhibits multiple morphologies when recrystallized from various solvents. After re-crystallized in ethanol, chloroform, toluene, and ethyl acetate, the crystalline materials are analyzed by X-ray diffraction (XRD) to determine differences in interplanar or lattice spacing (d-spacing) and diffraction patterns. All of the crystalline samples contain the same diffraction peaks except in varying intensities.

The present invention is directed to a crystalline form of 3-methylsulfonylpropionitrile having X-ray diffraction peaks at 13.9±0.1, 19.2±0.1, 20.0±0.1, 22.5±0.1, 23.2±0.1, 25.7±0.1, 28.1±0.1, 29.9±0.1, and 30.6±0.1 degrees 2θ, and wherein the most intense peak is the peak at 13.9±0.1 degrees 2θ.

The present invention provides pharmaceutical compositions comprising one or more pharmaceutically acceptable carriers and the crystalline form of 3-methanesulfonylpropionitrile, or a pharmaceutically acceptable salt, or solvate thereof. The active compound 3-methanesulfonylpropionitrile, or its pharmaceutically acceptable salt or solvate in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation.

The present invention provides a method of treating inflammation and/or pain. The active compound 3-methanesulfonylpropionitrile in a crystalline form can be used as is, or it can be administered in the form of a pharmaceutical composition that additionally contains a pharmaceutically acceptable carrier. The method comprise the steps of first identifying a subject suffering from inflammation and/or pain, and administering to the subject 3-methanesulfonylpropionitrile, in an amount effective to treat inflammation and/or pain. "An effective amount," as used herein, is the amount effective to treat a disease by ameliorating the pathological condition or reducing the symptoms of the disease.

The pharmaceutical compositions comprising 3-methanesulfonylpropionitrile and the method of treating inflammation and/or pain by administering 3-methanesulfonylpropionitrile have been described in details in co-pending application Ser. No. 13/324,777, which is incorporated herein by reference in its entirety.

The following examples further illustrate the present invention. These examples are intended merely to be illustrative of the present invention and are not to be construed as being limiting.

EXAMPLES

Example 1

Preparation of 3-Methylsulfonylpropionitrile (Two-Step Reactions)

Figure 1B:
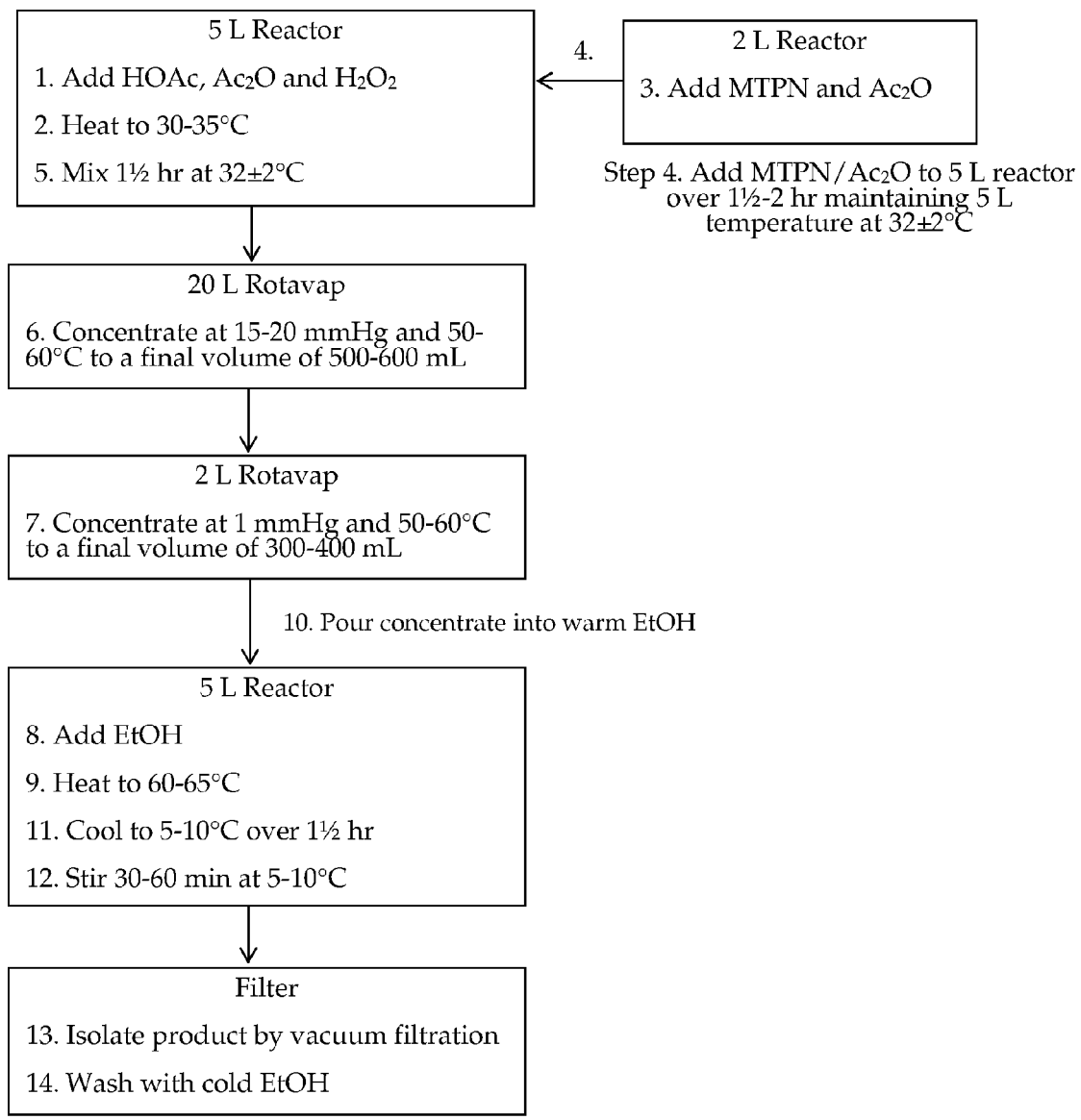
Figure 2A:
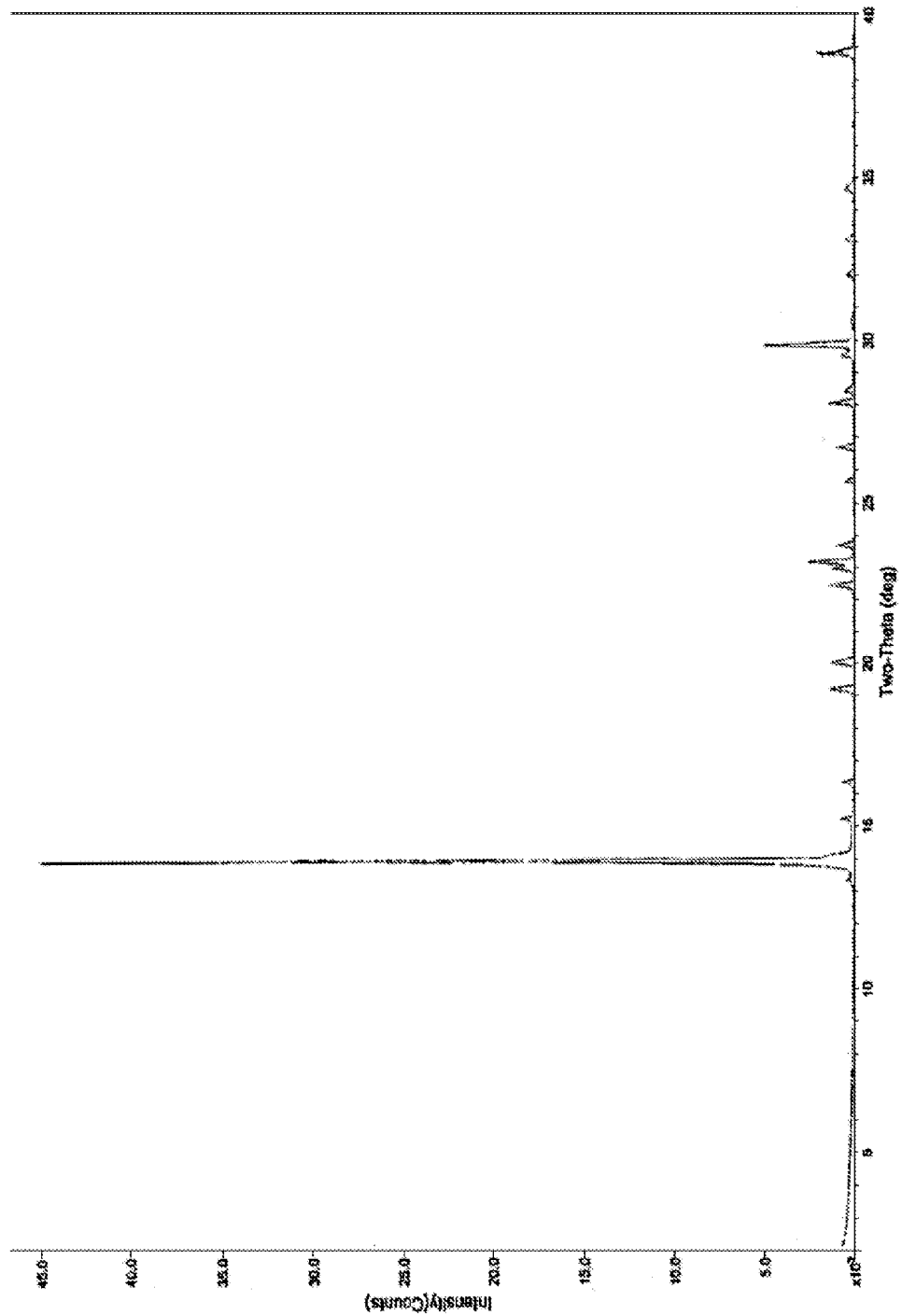
FIG. 2A-2D show the X-ray diffraction spectra of 3-methylsulfonylpropionitrile recrystallized in ethanol, chloroform, toluene, and ethyl acetate, respectively.
Figure 2B:
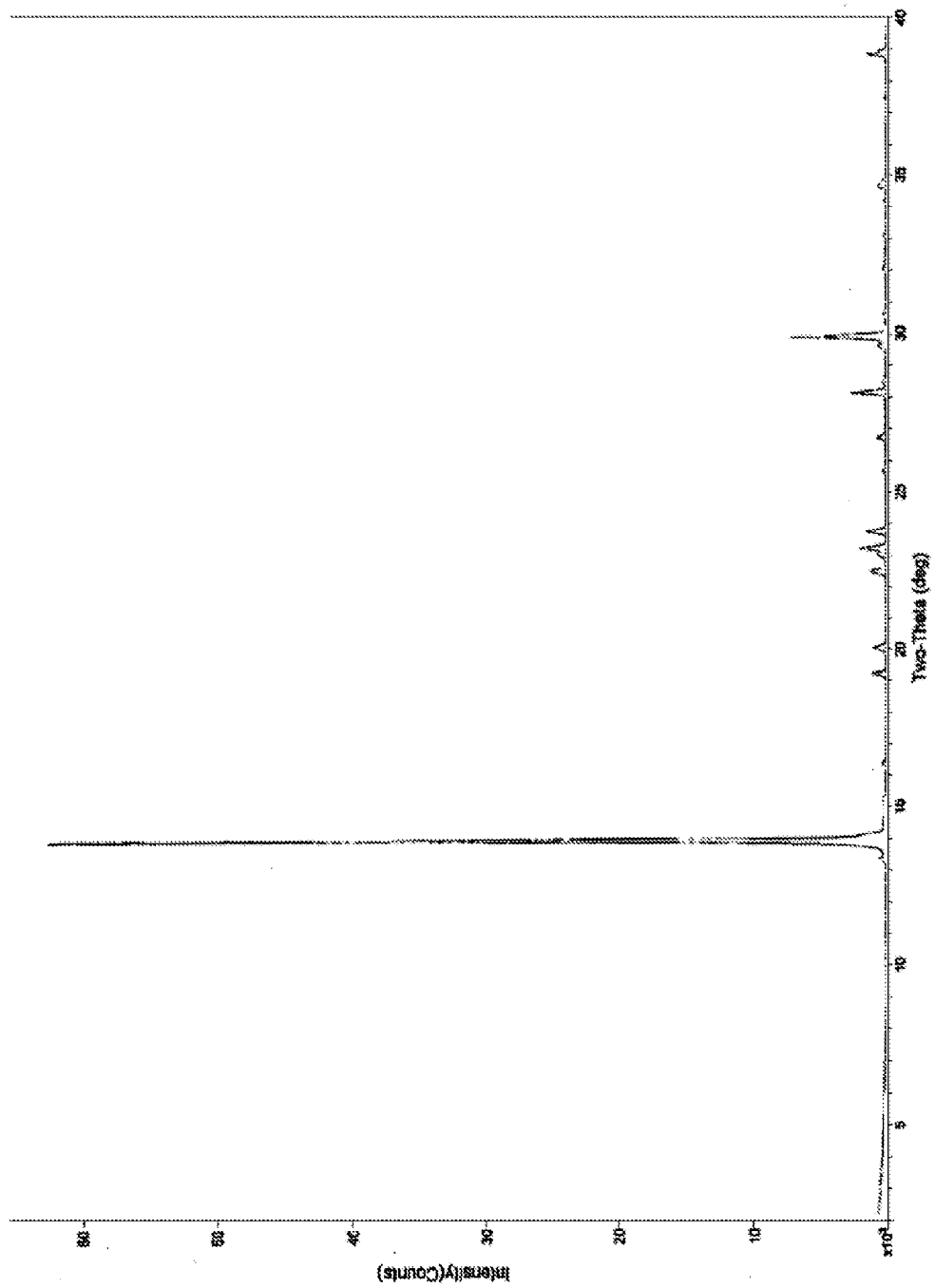
Figure 2C:
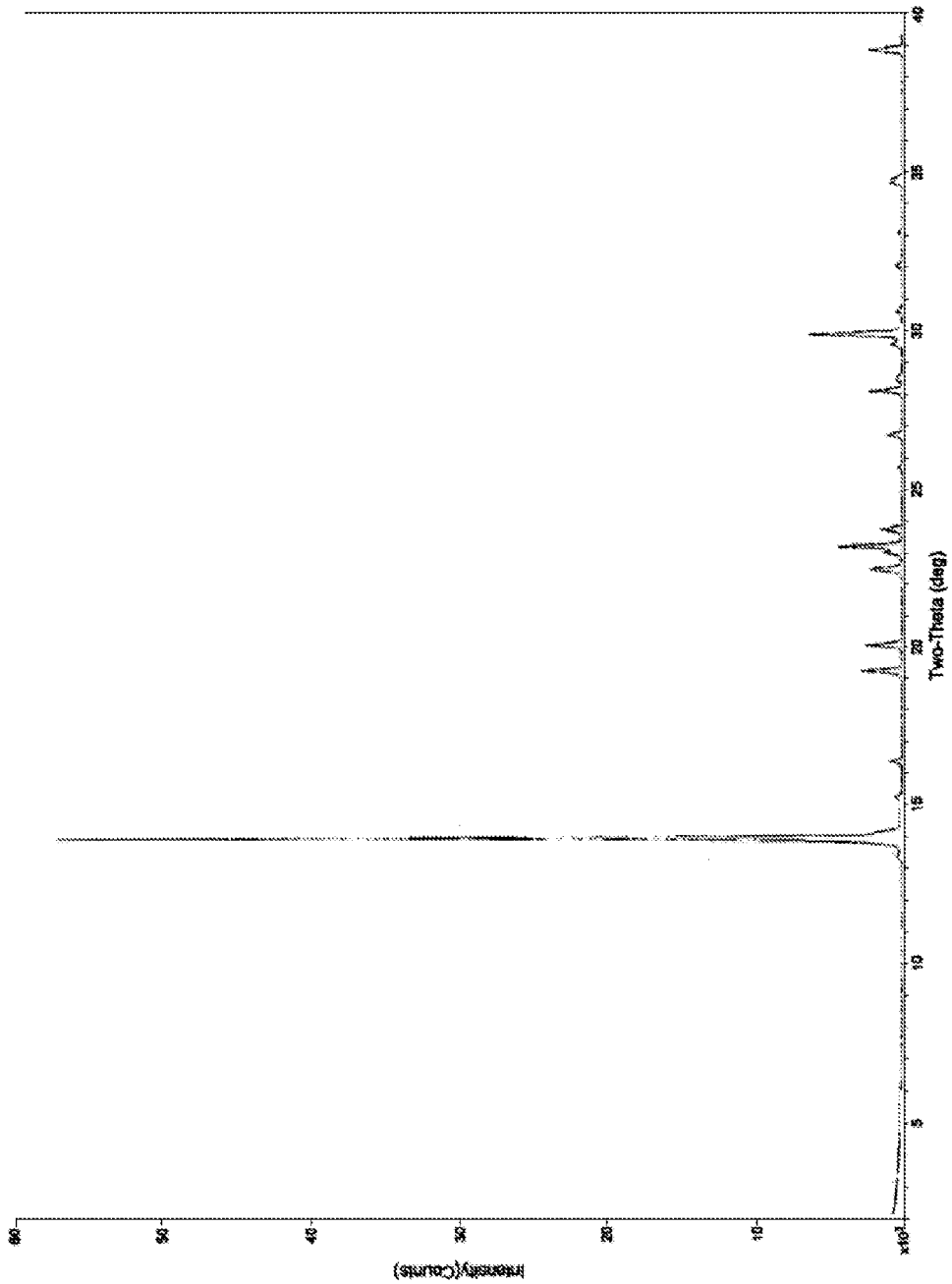
Figure 2D:
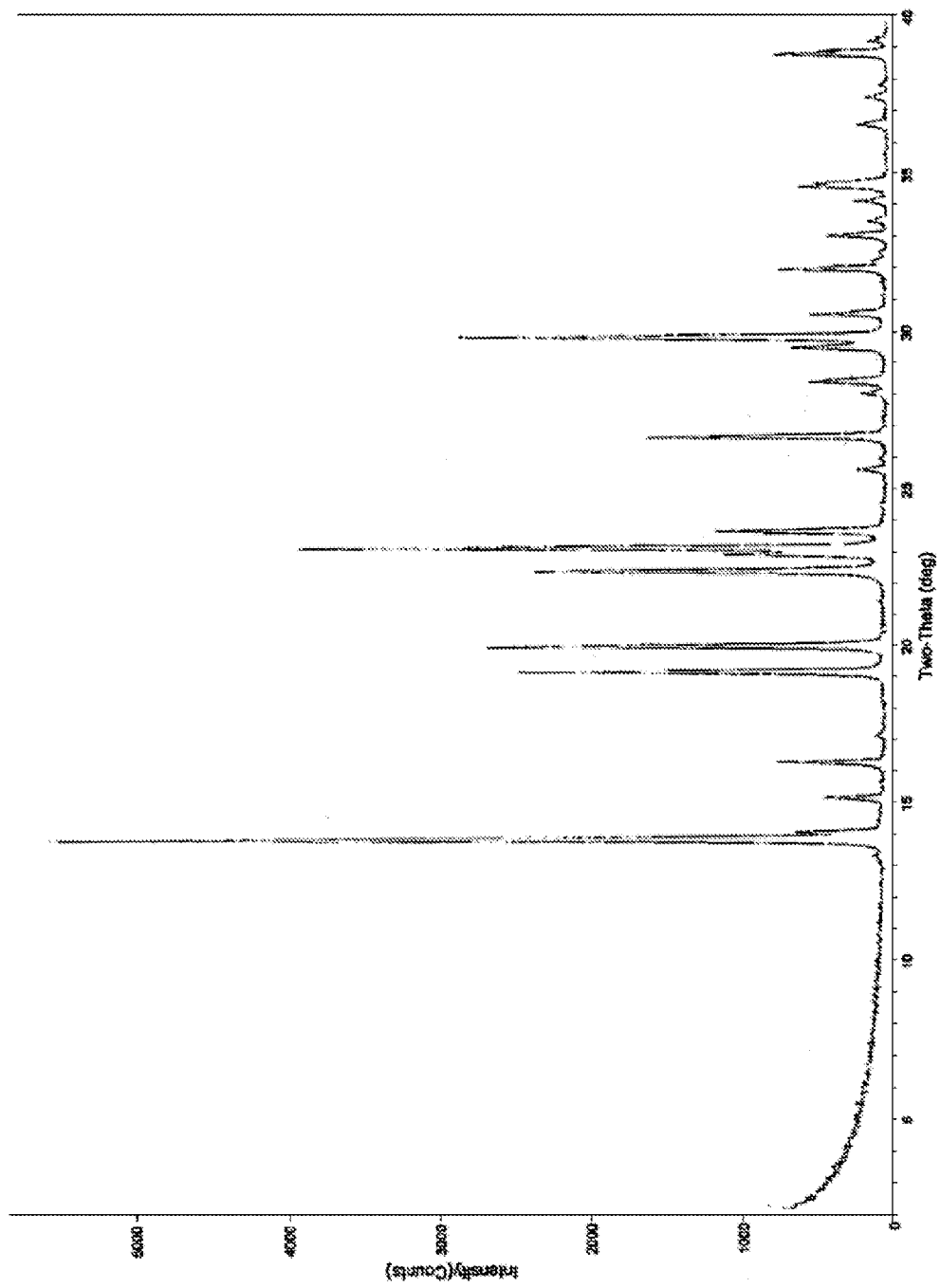

FIG. 1A-1C illustrate the process of Example 1.

a. Alkylation of Sodium Thiomethoxide by 3-Bromopropionitrile

1 L (~1110 g) of a 21% aqueous solution of sodium thiomethoxide (3.33 mol, obtained from Sigma-Aldrich) was added to a 2 L 3-neck round bottom flask equipped with mechanical stirrer and thermometer. The solution was cooled to 16±2° C. using an ice bath and 403.7 g (3.00 mol) of 3-bromopropionitrile (Sigma-Aldrich) was slowly added under moderate agitation over ~1 hr while maintaining the pot temperature at ≤20° C. throughout the addition. Stirring was continued for ~1½ hr at room temperature, and then the contents were transferred to a 2 L separatory funnel and allowed the resulting two-phase system to settle for ~15 minutes. The lower aqueous layer was discarded and the upper organic layer was transferred to a 500 mL beaker containing 60 g anhydrous sodium sulfate and stirred for ~1 hr. The dried methylthiopropionitrile was isolated by vacuum filtration to yield 279 g (2.75 mol) of a clear oily liquid.

b. Oxidation of Intermediate Methylthiopropionitrile (MTPN)

1 L acetic acid (17.4 mol), 500 mL acetic anhydride (5.30 mol) and 1 L 30% aqueous hydrogen peroxide (9.77 mol) were added to a 5 L jacketed reactor equipped with a mechanical stirrer, Julabo FP50-HL recirculator (set in external control mode) fitted with a Julabo PT100 remote temperature sensor inserted into one of the reactor lid ports to record and control the pot temperature. The reactor contents were slowly heated to 30-32° C. under moderate agitation. While the reactor was heating, the oil liquid methylthiopropionitrile obtained from (a) was mixed with 500 mL (5.30 mol) acetic anhydride, transferred to an addition funnel and fitted into one of the reactor lid ports. When the pot temperature stabilized at 30-32° C., the methylhtiopropionitrile/acetic anhydride solution was slowly added to the reactor over 1½-2 hr while maintaining a pot temperature of 30-34° C. Upon completion of the methylthiopropionitrile addition, the addition funnel was rinsed with 50 mL acetic anhydride and the reactor was then stirred for 10 minutes at 32±2° C. The reaction mixture (~3.5 L) was then transferred to a 10 L Büchi distillation flask and concentrated on a Büchi R220 rotary evaporation unit at 50-60° C., 20 mbar (15 mmHg) and rotation ~90 rpm until the bulk of the acetic acid with residual peroxide was distilled.

The material remaining in the 10 L distillation flask (~500-600 mL) was transferred to a 2 L 1-neck round bottom flask and concentrated to ~300-400 mL on a Büchi R124 rotary evaporator at 50-60° C. and 1 mmHg. The concentrate was added to the 5 L jacketed reactor with 2.7 L ethanol heated to 60-65° C. under moderate agitation. The mixture was slowly cooled to 5-10° C. over ~1½ hr to effect crystallization, stirred ~½ hr at 5-10° C. and isolated by vacuum filtration.

c. Recrystallization of Product 3-Methylsulfonylpropionitrile (MSPN)

The damp filter cake is added to a 5 L reactor with 2.7 L ethanol. The slurry was heated to 60-65° C. under moderate agitation and held until total dissolution (~5-10 min). The solution was slowly cooled to 5-10° C. over ~1½ hr to effect crystallization, stirred ½ hr at 5-10° C. and isolated by vacuum filtration. The isolated product was dried in vacuo at 30-35° C. to yield 310 g (2.33 mol, 78% yield from 3-bromopropionitrile) of a white crystalline material.

Example 2

Crystalline Form of 3-Methylsulfonylpropionitrile

3-Methylsulfonylpropionitrile (MSPN) was recrystallized from various solvents, e.g., ethanol, ethyl acetate, chloroform, and toluene.

MSPN recrystallized from ethanol was obtained from Example 1. The recrystallized
MSPN was dissolved by warming it to 65±2° C. in ethyl acetate (200 mg/mL), chloroform (200 mg/mL), and toluene (about 35 mg/mL). Once dissolved, the samples were allowed to equilibrate at room temperature (about 20° C.) for about 1 hour at which point crystals were observed in all three of the samples. The samples were then held in −20° C. storage, to maximize yield, and filtered the following day. The filtered samples were dried in vacuo at room temperature for about 1½ hr before being packaged and sent for XRD analysis.

To measure the diffraction pattern of crystal structures, the plane distance of the crystals and the intensity of diffraction rays, powder X-ray diffraction analysis was carried out. FIG. 2A-2D show the X-ray diffraction spectra of 3-methylsulfonylpropionitrile recrystallized in ethanol, chloroform, toluene, and ethyl acetate, respectively.

Characteristic peaks appearing in the X-ray diffraction spectra of MSPN recrystallized in ethanol, chloroform, toluene, and ethyl acetate, are shown in Table 1, wherein "2θ" represents diffraction angle, "d" represents the distance between crystal planes. The analysis was carried out using ARL X' TRA Powder Diffractometer (Thermo Fisher).

TABLE 1

XRD Data Summary

| 2-Θ (±0.05) | d(Å) (±0.01) | Area ratio to primary 2Θ value | | | |
|---|---|---|---|---|---|
| | | Ethanol | Chloroform | Toluene | Ethyl Acetate |
| 13.94 | 6.34 | 100.0% | 100.0% | 100.0% | 100.0% |
| 19.22 | 4.61 | 3.9% | 2.5% | 6.3% | 36.7% |
| 20.04 | 4.43 | 4.5% | 2.5% | 5.8% | 45.1% |
| 22.46 | 3.96 | 4.8% | 3.2% | 6.2% | 46.1% |
| 23.18 | 3.83 | 7.6% | 4.7% | 10.8% | 71.5% |
| 25.66 | 3.47 | 1.4% | 0.5% | 0.7% | 3.7% |
| 28.08 | 3.17 | 3.8% | 4.4% | 4.4% | 2.9% |
| 29.86 | 2.99 | 15.2% | 15.2% | 16.1% | 51.7% |
| 30.58 | 2.92 | 0.3% | 0.6% | 1.0% | 7.7% |

The XRD data show that MSPN recrystallized in ethanol, chloroform, and toluene exhibited almost identical diffraction patterns with primary 2θ values of 13.94 (100%) and 29.86 (15.2-16.1%). The MSPN recrystallized from ethyl acetate exhibited a more diverse pattern; although it also had 2θ 13.935 as the most intense peak, it had different intensities of several other peaks when comparing with other re-crystallized form. Table 1 showed that all of samples contained the same diffraction peaks except in varying intensities.

The ethyl acetate recrystallized MSPN was further evaluated to determine if solvation could be attributable to the variation in peak intensities. Analysis for residual solvents by Gas Chromatography equipped with Flame ionization detection using standard methodology (e.g.USP method <467>) indicated 4100 ppm (0.41%) ethyl acetate (about 160:1 mole ratio MSPN to solvent), which suggests that the difference in peak intensities of the diffraction pattern is not likely due to solvation. The ethyl acetate recrystallized MSPN and the ethanol recrystallized MSPN were further dried (in vacuo at 35° C., 16 hr) and resulted in 0.53% LOD (loss on drying) and 0.42% LOD respectively. These samples were reanalyzed by XRD to determine the impact on crystal structures. The spectra indicate that additional drying had no impact on the diffraction pattern of these materials.

Example 3

Preparation of 3-Methylsulfonylpropionitrile (One-Step Reaction)

1818.3 g sodium methylsulfinate (Oakwood Products, Inc., product# 1284, 16.5 mol) and 12.5 L ethanol (Pharmco-Aaper, Product # 241000200) were added to a 20 L jacketed reactor equipped with a mechanical stirrer with tachometer, Julabo FP50-HL recirculator fitted with a Julabo PT100 remote temperature sensor inserted into one of the reactor lid ports to record and control the pot temperature and a condenser equipped with a recirculating chiller. The slurry was mixed under moderate agitation and the Julabo was set to heat the batch to 78±3° C. in external (batch) control mode. The addition of 2652.9 g (19.7 mol) 3-bromopropionitrile (Far Chemical, Inc.) was conducted as the batch was heating. The contents of the reactor were held at 79±2° C. for 16 hours. The reactor was slowly cooled from 79° C. to 5° C. over a two-hour period. The batch was held for ~30 minutes at 5±5° C. prior to isolation by vacuum filtration. The filter cake was washed with 2.0 L ethanol and allowed to hold under vacuum ~30 minutes prior to removal of the solids from the filter and collection of 4113.6 g damp filter cake.

15.0 L acetone was added to the 20 L jacketed and heated to 21±3° C. under moderate agitation. The damp filter cake was added to the reactor and allowed to mix for 1 hour. The insoluble salts were isolated by vacuum filtration and the filter cake was washed with 2.0 L acetone. The filtrate (~15 L) was slowly added to a 20 L Büchi distillation flask attached to a Büchi R220 rotary evaporation unit at 50-60° C., 200 mbar (150 mmHg) and rotation ~90 rpm. The filtrate was gradually added as the distillation of acetone commenced and the distillation flask was concentrated to dryness over ~3-4 hours.

During the distillation step, the 20 L reactor was cleaned, charged with 17.3 L ethanol and heated to 65-70° C. under moderate agitation. The concentrated solids were scraped from the 20 L distillation flask and added to the hot ethanol in the 20 L reactor. The reactor was cooled to 55±4° C. to effect crystallization. The mixture was slowly cooled to 5-10° C. over ~1½ hr to affect crystallization, stirred ~½ hr at 5±4° C. and isolated by vacuum filtration. The damp filter cake was washed with 2.0 L ethanol. The isolated product was dried in vacuo at 30-35° C. to yield 1931.2 g (14.5 mol, 88% yield from sodium methylsulfinate) of a white crystalline material.

Example 4

Preparation of 3-Methylsulfonylpropionitrile, Alternative Procedures (One-Step Reaction)

Figure 3A:
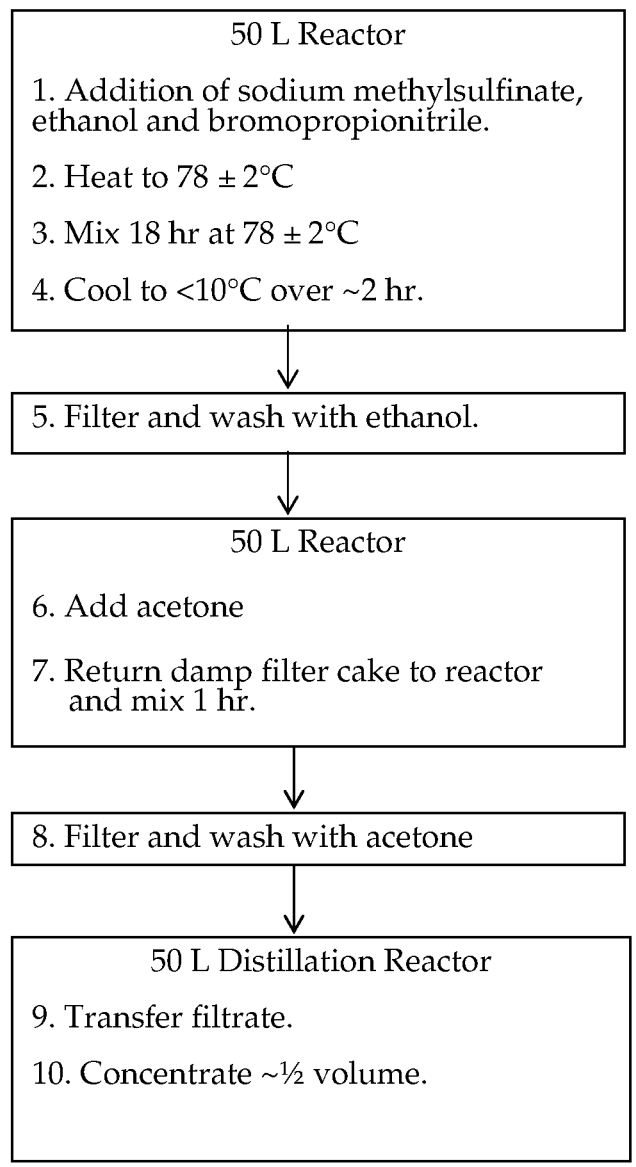
FIG. 3A-3B illustrate a flow chart for preparing 3-methylsulfonylpropionitrile according to Example 4.
Figure 3B:
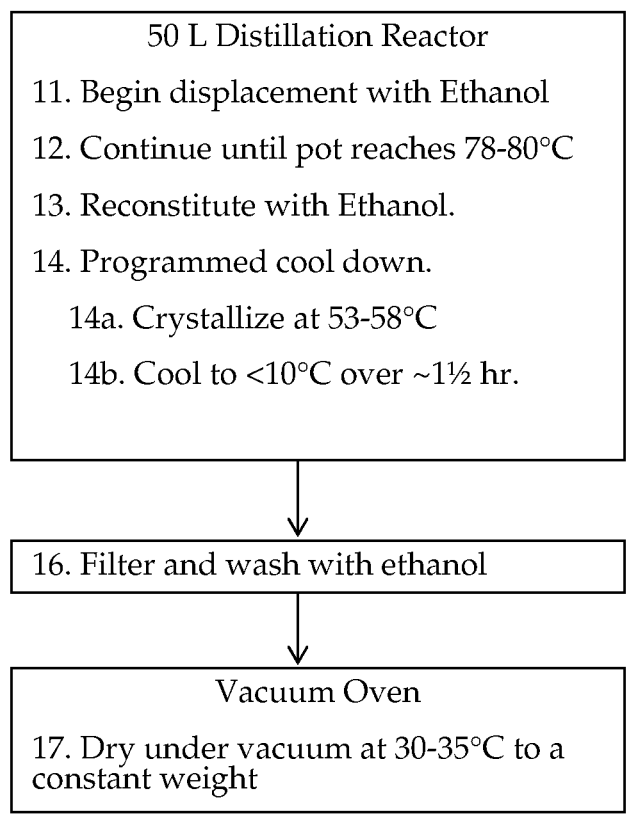

FIG. 3A-3B illustrate the process of Example 4.

Sodium methylsulfinate and ethanol are added to a 50 L jacketed reactor and the batch is heated to 78±3° C. The addition of bromopropionitrile is conducted as the batch is heating. The reactor contents are held at 79±2° C. for 16 hours. The reactor is slowly cooled, by programming the temperature control system, from 79° C. to 5° C. over a two-hour period. The batch is held for about 30 minutes at 5±5° C. prior to isolation by vacuum filtration. The filter cake is washed with ethanol and allowed to hold under vacuum for about 30 minutes prior to removal of the crude solid from the filter.

Acetone is added to the 50 L jacketed reactor and heated to room temperature (21±4° C.) under moderate agitation. The damp filter cake is added to the reactor and allowed to mix for 1 hour. The insoluble salts (sodium bromide) are isolated by vacuum filtration and the filter cake is washed with acetone. The acetone filtrates (product solution) are added to a second 50 L jacketed reactor configured as a distillation vessel. The distillation reactor is heated to 60±5° C. and acetone distillate is collected in the distillate receiver. The contents of the distillation reactor are concentrated to approximately half of the initial volume. Ethanol is added in increments to maintain the reactor at approximately half volume while maintaining a temperature controller set point of 5-15° C. above the pot temperature. The displacement of acetone with ethanol is continued until the pot temperature levels off at 76-80° C. Ethanol is added to bring the reactor to full volume. The reactor is slowly cooled, by programming the temperature control system, from 79° C. to 5° C. over a two hour period. The batch is held for ~30 minutes at 5±5° C. prior to isolation. The product is isolated by vacuum filtration and washed with ethanol.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method for preparing 3-methylsulfonylpropionitrile, comprising:
    (a) reacting 3-bromopropionitrile and sodium methylsulfinate in an organic solvent to obtain crude 3-methylsulfonylpropionitrile in a solid form, and
    (b) removing a byproduct sodium bromide.

2. The method according to claim 1, further comprising a step (c) after step (b):
    (c) purifying 3-methylsulfonylpropionitrile.

3. The method according to claim 1, wherein the step (a) comprises:
    (i) reacting 3-bromopropionitrile and sodium methylsulfinate in the organic solvent at ≥40° C. for at least 8 hours, and
    (ii) cooling the reaction mixture to ≤15° C., and
    (iii) isolating 3-methylthiopropionitrile in the solid form from the cooled reaction mixture.

4. The method according to claim 1, wherein the organic solvent comprises ethanol, methanol, propanol, isopropanol, butanol, or a mixture thereof.

5. The method according to claim 4, wherein the organic solvent comprises ethanol.

6. The method according to claim 1, wherein 3-bromopropionitrile and sodium methylsulfinate are reacted in an ethanol solvent at 75-83° C.

7. The method according to claim 1, wherein the byproduct is removed by:
    (i) adding acetone to the solid form of the step (a) to dissolve the solid and form a solution,
    (ii) filtering the solution of (i) to remove the insoluble byproduct, and
    (iii) collecting the filtrate.

8. The method according to claim 7, wherein 3-methylsulfonylpropionitrile is purified by drying the filtrate of (iii), dissolving the dried material in a second organic solvent, and crystallizing 3-methylsulfonylpropionitrile.

9. The method according to claim 8, wherein the second organic solvent is selected from the group consisting of ethanol, methanol, propanol, isopropanol, butanol, ethylacetate, or a mixture thereof.

10. The method according to claim 9, wherein the second organic solvent is ethanol.

* * * * *